(12) United States Patent
Fuhr et al.

(10) Patent No.: US 8,586,341 B2
(45) Date of Patent: Nov. 19, 2013

(54) METHOD AND DEVICES FOR NON-TRAUMATIC MOVEMENT OF A PROBE THROUGH BIOLOGICAL CELL MATERIAL

(75) Inventors: Günter R. Fuhr, Berlin (DE); Heiko Zimmermann, Kronberg (DE)

(73) Assignee: Fraunhofer-Gesellschaft zur Forderung der Angewandten Forschung E.V., Munich (DE)

( * ) Notice: Subject to any disclaimer, the term of this patent is extended or adjusted under 35 U.S.C. 154(b) by 1026 days.

(21) Appl. No.: 10/546,023

(22) PCT Filed: Dec. 2, 2003

(86) PCT No.: PCT/EP03/13582
§ 371 (c)(1),
(2), (4) Date: Sep. 12, 2005

(87) PCT Pub. No.: WO2004/074426
PCT Pub. Date: Sep. 2, 2004

(65) Prior Publication Data
US 2006/0134600 A1    Jun. 22, 2006

(30) Foreign Application Priority Data
Feb. 21, 2003  (DE) .................................. 103 07 487

(51) Int. Cl.
*C12N 1/00* (2006.01)
*C12N 5/02* (2006.01)
*C12M 1/00* (2006.01)

(52) U.S. Cl.
USPC .......................... 435/243; 435/325; 435/285.3

(58) Field of Classification Search
USPC ...................... 435/243, 325, 285.3
See application file for complete search history.

(56) References Cited

U.S. PATENT DOCUMENTS
5,877,008 A    3/1999  Remenyik et al.

FOREIGN PATENT DOCUMENTS

| CH | 652933 A5 | 12/1985 |
|---|---|---|
| DE | 2501270 B1 | 8/1975 |
| DE | 19714987 C1 | 9/1998 |
| EP | 0539888 A1 | 5/1993 |
| WO | WO 9964580 | * 12/1999 |
| WO | 03047738 A2 | 6/2003 |

OTHER PUBLICATIONS

Andreas H. Guse et al. "Ca21 Entry Induced by Cyclic ADP-ribose in Intact T-Lymphocytes" The Journal of Biological Chemistry, vol. 272, No. 13, Issue of Mar. 28, pp. 8546-8550, 1997.*
P.C. Wilkinson "Assays of leukocyte locomotion and chemotaxis" Journal of Immunological Methods 216_1998.139]153.*
Abercrombie, et al., "The Locomotion of Fibroblasts in Culture", Experimental Cell Research 67 (1971), pp. 359-367.
Cramer, "Organization and polarity of actin filament networks in cells: implications for the mechanism of myosin-based cell motility", Biochem. Soc. Symp. 65, pp. 173-205 (1999).
Fuhr et al., "Cell Traces-Footprints of Individual Cells during Locomotion and Adhesion", Biol. Chem., vol. 379 (1998), pp. 1161-1173.
Alberts et al., "Molecular Biology of the Cell", pp. 972-978 (4th ed., 2002).
Sakai et al., Abstract of JP 2000098258, Jul. 4, 2000.
Sogawa et al., Abstract of JP 03247268, May 11, 1991.
WO 84/04686 A1 is a counterpart of CH 652933 A5 having an English-language abstract on its cover page.
DE 2501270, An English-language abstract is attached.
WO 98/44972 A3 is a counterpart of DE 19714987 C1 having an English-language abstract on its cover page.
(H. Thielecke et al. Gentle cell handling with an ultra-slow instrument: creep-manipulation. of cells. Microsyst Technol (2005) 11: 1230-1241.

* cited by examiner

*Primary Examiner* — Jon P Webber
*Assistant Examiner* — Larry Moore
(74) *Attorney, Agent, or Firm* — Caesar, Rivise, Bernstein, Cohen & Polotilow, Ltd.

(57) ABSTRACT

A method for moving a probe (10, 91) through a cell material (20), which is formed from biological cells (21), is described, the probe (10) displacing the cells (21) without injury. A probe (10, 91) for performing the method and a cell manipulator, which is equipped with at least one probe of this type, are also described.

19 Claims, 5 Drawing Sheets

METHOD AND DEVICES FOR NON-TRAUMATIC MOVEMENT OF A PROBE THROUGH BIOLOGICAL CELL MATERIAL

BACKGROUND OF THE INVENTION

The present invention relates to methods for moving a manipulation and/or examination device, particularly a probe, through biological cell material which is formed from biological cells, manipulation and/or examination devices which are adapted for performing methods of this type, cell manipulators which have at least one manipulation and/or examination device of this type, and applications of the cited methods.

In medicine, biotechnology, and biochemistry, there are numerous methods in which biological cells are examined or processed or used for examining or processing biological materials. For example, for medicinal cell therapy, cells are taken from an animal or human subject, treated, collected, sorted, and/or cultivated outside the subject body, in order to subsequently return specific cells or cell groups into the subject. Special advantages are expected from medicinal cell therapy using stem cells, since these have the capability of differentiation into nearly all cell types of the body and therefore represent candidates for individual cell therapies and for in vitro regeneration of tissue. It is currently assumed that adult or embryonic stem cells are capable, under suitable conditions, of nearly all cell performances of the body and therefore also for producing or regenerating different tissues. There is a strong interest in safe and reproducible handling of biological cells.

The essential objects in the examination or manipulation of biological cells, particularly in connection with medicinal cell therapy and tissue engineering, are that at predefined locations, for example, in the tissue or in a cell composite, individual, previously selectable cells or cell groups are to be able to be inserted or removed or defined measurements are to be able to be performed with a precision in the µm range. These objects must be able to be achieved with high reproducibility, controllability, and precision without impairing or damaging the cells or the tissue. Until now, these requirements have not been satisfactorily fulfilled. For example, in animal experiments, in spite of identically performed methods, e.g., for the injection of cells into diseased tissue, contradictory results have been achieved. It has been determined that the positive course of a tissue regeneration is sensitively dependent on the method conditions, particularly on the type of the injection, the number of cells or substances introduced, and the injection tools used. In numerous experiments known from practice, the desired regeneration or new formation of a cell or tissue type did not occur, but rather an induction of tumors, for example. It is assumed that the induction of tumors as the uncontrolled cell reproduction of stem cells is encouraged through physical, chemical, or mechanical external influences at the injection location. These influences may not be reproducibly set or at least detected using the conventional injection technologies.

Figure 9:
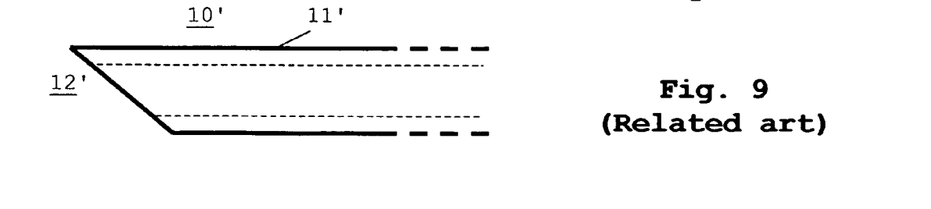
FIG. 9 shows the tip of a conventional injection needle.

Until now, cannulas or hypodermic needles have been used as the injection tools. For example, FIG. 9 shows the tip of a conventional injection cannula 10' in an enlarged side view. The injection cannula 10' has a hollow cannula body 11', whose free end 12' is beveled and possibly ground to form a tip. In order to form the straightest and most reproducible injection channel possible into a tissue, the cannula body 11' is implemented as thin as possible and the end 12' is implemented as pointed and sharp. Although the conventional injection cannula 10' for precision applications has an extremely small diameter in the submillimeter range and the end 12' runs to a sub-µm tip, injury-free insertion into a tissue is basically excluded in the conventional application of the cannula. As soon as the tip hits cells at the high injection velocity currently used in a tissue, these are mechanically injured, crushed or torn, for example.

Performing subcutaneous endoscopy by inserting endoscopes or auxiliary devices into subcutaneous tissue is generally known from medical technology. However, subcutaneous endoscopy is always connected with injury to tissue and blood vessels and is therefore unsuitable for the biotechnological processing of cell materials.

The problems cited in cell therapy and the currently partially unsatisfactory results in tissue engineering currently represent the most important restrictions and delays of a broad application of these methods in biotechnology and medicine.

The object of the present invention is to provide improved methods for moving a foreign body, particularly a manipulation and/or examination device (or probe) through a cell material which is formed from biological cells, using which the problems of the conventional injection methods are countered and which are suitable in principle for fulfilling the requirements listed above in cell technologies. It is particularly the object of the present invention to provide improved methods for inserting a manipulation and/or examination device into cell tissue or cell groups, using which cells or other substances are insertable into the cell material, cells or cell components are removable from the cell material, and/or measurements are performable in the cell material. It is also the object of the invention to provide improved manipulation and/or examination devices for performing methods of this type and injection devices equipped with at least one device of this type, using which the disadvantages of conventional injection tools are overcome. A further object of the present invention is to specify novel applications of the insertion of probes into cell material.

SUMMARY OF THE INVENTION

In regard to the method, the present invention is based on the general technical teaching of moving a manipulation and/or examination device through a cell material having biological cells in such a way that the probe displaces the cells without injury. The probe is actuated in the cell material in such a way that the cells are pushed apart or separated from one another by the surface of the probe, so that space is provided for the probe, the cells remaining unchanged in their physical and chemical state during the displacement or separation. Injury-free displacement of cells is particularly provided if, during the movement of the probe, the cells in direct contact with the probe body or cells lying deeper in the cell material are deformed or change their spatial position, but do not release any chemical signals in the form of messenger substances or substance secretions.

In this case, cell material is generally understood as an accumulation of cells which is connected with its environment via adhesion contacts (macromolecular chemical bonds, no van der Waals bonds). The cell material is, for example, a composite or an aggregation of individual cells, a tissue (combination of identical differentiated cells), or an organ. The non-liquid composite of individual cells may contain additional synthetic components, such as a synthetic matrix or carrier material. A broader range of applications of the present invention thus advantageously results. The probe is generally a foreign body or object made of a material which may be delimited in relation to cell material, preferably having a fixed surface. The probe may particularly comprise a manipulation and/or examination device, such as an injection capillary or electrical lines, which may be inserted into the cell material (for example, brain).

The present invention is particularly based on the following considerations of the inventors. It was first recognized that the reactions of, for example, cells injected into a tissue or a cell composite, which currently have differing results, are caused because cells in the existing cell material are injured or destroyed by the insertion of an injection tool and wound effects are thus caused. In the event of a cell or tissue injury, chemical signals (emission of molecular messenger substances) or cellularly carried processes are generated, such as fibroplastic immigration, fibronectin secretion, or the like. The reaction of injured cells influences the effect of the injected cells or additives. For example, stem cells behave differently in the environment of a cell injury than stem cells in intact cell material. Secondly, the inventors have found that contrary to current expectations, even adhesively bonded cells may be spatially displaced without injury. This allows the mechanical insertion of probes into cell material. The cells remain uninjured as the probe moves through the cell material if the advance velocity is sufficiently low that the adhesion contacts between the cells detach in natural ways, i.e., ways which do not influence or destroy the cells, and may reform in the changing environment.

The above-mentioned requirements may be completely fulfilled by the movement of the sample using injury-free displacement of cells. Neither the target tissue nor the individual cells or substances to be used are damaged or impaired. The physical, chemical, and mechanical state of the cells may be completely characterized. Damaging contacts between cells and surfaces of foreign bodies are avoided, cellular signals due to surface contacts are suppressed. Through the injury-free movement, the cell manipulation is performed extremely carefully. The probe may be guided accurately to a specific location in the cell material. It is also especially advantageous that restrictions on the size of the sample, as exist in conventional injection cannulas, are overcome. A tool moved through the cell material according to the present invention allows a precise and reproducible detection of the number and type of the cells or additives introduced into the cell material.

According to a preferred embodiment of the present invention, the probe is moved at a advance velocity which is lower than or equal to a reference velocity that is determined by the physiological binding rate for natural cell movement of biological cells (binding velocity of the cells). The natural cell movement (cell locomotion) comprises the change in location of a complete cell on a fixed surface or in cell material by rearranging adhesion contacts of cell organs (membrane organs, for example, membrane protuberances), as are described, for example, by M. Abercrombie et al. in the publication "The Locomotion Of Fibroblasts In Culture" ("Experimental Cell Research", Vol. 67, 1971, pages 359-367) and by L. P. Cramer in the publication "Organization and polarity of actin filament networks in cells: implications for the mechanism of myosin-based cell motility" ("Biochem. Soc. Symp." Vol. 65, 1999, pages 173-205).

When setting the advance velocity, the probe may advantageously be moved without injury through cells in a naturally provided composite. The advance velocity is adapted to the cell movement occurring permanently in cell tissue. For example, it is known that specific types of immune cells (e.g., macrophages), may even move through dense tissue by displacing existing cells. The inventors have found that this displacement movement may surprisingly also be implemented using probes which are significantly larger than immune cells and have macroscopic dimensions in the submillimeter to centimeter range, if the cited advance velocity is set. During the probe movement, macromolecular bonds running between the cells (for example, membrane-related macromolecules of the integrin and cadherin families) are separated and relinked to the probe surface, for example.

The physiological reference velocity is known per se (see, for example, G. Fuhr et al. in "Biol. Chem.", 1998, Vol. 379, pages 1161-1173) or measurable on animal or human cells. The binding rate of interest may be derived by measuring the dynamics of adhesion patterns of individual cells on artificial surfaces, for example.

If the probe is subjected to a permanently acting advance force, the movement of the probe at the desired advance velocity may advantageously be performed even with the slightest application of force. This allows the use of drive devices having low output. If the advance force is formed by a mechanical pressure force, advantages for the transmission of the advance force to the probe may result. If the advance force is formed by forces in electrical or magnetic fields, advantages may result for the construction of an injection device, since the advance forces may be exerted via remote action.

According to a special embodiment of the invention, the advance force may be formed by intercellular forces. The probe may travel through the cell material without an external drive by the effect of the adhesion bonds existing in the cell material. For example, if the probe has a stronger tendency to form adhesion bonds on one side than on another side due to a surface treatment, the probe may be driven forward by the generation of the adhesion bonds, which may be also supported if necessary by the shape of the probe and/or by the other above-mentioned advance forces.

According to a preferred embodiment of the invention, the probe is moved in a direction which runs parallel to the alignment of an oblong shape of the probe. In this case, advantages may result in regard to the injury-free displacement of the cells. The displacement must only occur on the front side of the probe, which represents a very small area sector in comparison to the remaining surface. Furthermore, this embodiment has the advantage of being compatible with conventional injection technologies using syringes, cannulas, or capillaries. The probe may be combined with devices available per se for the manipulation of cells or cell suspensions. In particular, it is made possible for a substance to be supplied into the cell material using the probe. For this purpose, liquid delivery devices known per se, such as pumps or the like, may advantageously be used.

Alternatively, a lateral movement of the probe may be provided, in which a movement direction is set that deviates from the e.g. oblong shape of the probe. A lateral movement of the probe may generally also comprise a radial expansion of the probe body in the cell material (expansion movement).

Special advantages for the intended applications in biotechnology and medicine may result if at least one cell is supplied into the cell material using the probe, since the cell finds the cell material in a physiologically uninjured state upon its injection. The at least one cell is embedded in the interior of the uninjured cell material. In particular, stem cells may be implanted in tissue in order to cause a tissue-specific differentiation of the stem cells. Degenerations or tumor formations may be suppressed.

The method according to the present invention advantageously also allows the injection of biological cells in a frozen state. After cryopreservation, one or more cells may be embedded in the frozen state in the cell material and thawed there. The cellular processes are started immediately under the physiological conditions in the cell material during the thawing.

According to an alternative embodiment of the present invention, at least one cell is removed from the cell material using the probe. The probe forms a biopsy tool. In this embodiment, advantages may result for obtaining unmodified, physiological cells.

The principle of injury-free displacement of cells according to the invention allows the use of probes having dimensions which also allow an integration of sensors. Therefore, according to a variant of the present invention, properties of the cell material, of injected cells, or of extracted cells may be detected using the probe.

Particular advantages of the present invention result if the advance velocity of the probe is selected in a velocity range from 0.1 µm/h to 1 mm/h, preferably in a range from 1 µm/h up to 500 µm/h. The bonding rates of the formation and breakdown of macromolecular bonds, which are conventionally mediated by membrane-related macromolecules of the integrin and cadherin families, lie in this velocity range. The preferred velocity ranges correspond to the velocities of the cell movement of fibroplasts, macrophages, lymphocytes, chondrocytes, or tumor cells in particular. If a advance velocity this low is set, the position of the probe may advantageously be set with a high precision of up to +/−1 µm. The advance velocities in the cited ranges correspond to the active endogenic movement velocities of cells in and on tissue. The movement of the probe thus causes a permanent formation and restructuring of the cells in the direct environment of the probe surface, displacement of the cells being encouraged by the permanently acting advance force.

Different movement types of the probe, particularly movements with a net advance or a net retraction, discontinuous movements or movements decomposed into sections, oscillatory, uniform, or accelerated movements may advantageously be implemented depending on the application.

Particular advantages may result if the method according to the invention is executed on cell material which is located outside an animal or human organism. The cell material may be positioned under suitable cultivation conditions on a fixed carrier, which applies the counterforce to the exertion of the advance force. The cell material and the probe may be positioned with high precision.

Alternatively, the cell material may be located in the composite in a living organism. The probe may, for example, be inserted as an examination probe, biopsy tool, or injection tool into tissue. The insertion occurs, because of the low advance velocity, in a state in which the affected tissue is held fixed in one location on a carrier, e.g., with the surrounding part of the organism. The use of an anesthetic is preferred for the immobilization, but is not absolutely necessary in regard to the freedom from injury of the method, however.

A further subject of the invention is a manipulation and/or examination device, particularly a probe or an examination, biopsy, and/or injection tool, which is designed for the purpose of being at least partially inserted into the cell material. The probe has a probe body which is movable through the cell material and has a rounded or flattened surface on at least one front side, which, during a movement of the probe through the cell material, forms a forward end, front end, or forward displacement or separating part in relation to the movement direction. The front side has a contour which is free of pikes, steps, edges, blades, and the like. The front side has a mathematically continuous curved contour which may be described as a sector of a surface of a sphere, an ellipsoid, a toroid, or a superposition of these. Providing the rounded or flattened surface on at least one front side has the advantage that upon insertion of the probe into the cell material according to the method according to the invention, injuries are avoided, since the advance force acts uniformly over the entire rounding of the front side. Local pressure increases on individual cells, which are caused by pikes or steps, for example, may be excluded using the tool according to the invention. Therefore, the probe differs in principle from conventional injection tools, such as syringe needles, in which the injury is necessarily provided by conducting a cut through the cell material.

According to a preferred embodiment of the invention, the probe front side has a local radius of curvature which is larger than 10 µm in individual regions of the rounded surface. Therefore, the rounded or flattened surface is larger than the types of cells in the conventionally treated cell materials, particularly types of cells in tissue. Therefore, the probability of injury during the movement of the probe is reduced. Special advantages may result with a local radius of curvature which is larger than 20 µm, preferably larger than 0.1 mm. For the application in cell cultures, the radius of curvature is smaller than 5 mm, preferably smaller than 2 mm. Alternatively, it may be very large, so that the front side is essentially flattened.

According to a further preferred embodiment of the present invention, the rounded surface is formed by a material (bonding material) which encourages adherent adhesion of cells to the surface. The bonding material forms the probe body, at least the front of the probe body, or a coating at least on the front of the probe body. It is made of, for example, fibronectin or collagen. This embodiment of the invention may have advantages in regard to elevation of the bonding speed during the displacing movement of the probe through the cell material. The bonding material may alternatively have characteristic structure sizes in the sub-µm range, due to roughening, so that the bonding of the cell material to the probe is encouraged. Like the rounding of at least one surface, the use of an adhesion-encouraging material also represents an essential and basic difference of the tool according to the invention in relation to conventional injection needles.

According to an advantageous variant of the invention, at least one functional part is integrated into the probe body. The functional part generally represents a structural component of the probe body which is designed for specific technical functions of the probe. The functional part is advantageously integrated into the probe body, so that the injury-free displacement movement is not disturbed.

According to a preferred embodiment of the invention, the functional part comprises a cavity which is adapted for receiving and/or conducting cells or additives into or out of the cell material. The cavity formed in the probe body has at least one opening on one side which is formed in a surface of the tool body. On the other hand, a connection of the cavity to an external sample reservoir may be provided.

Furthermore, the functional part may comprise at least one sensor in the probe body which is adapted for detecting chemical or physical properties of cells or substances in the cell material or in the interior of the probe body. If the at least one sensor is positioned in the cavity of the probe body, advantages for monitoring an injection or a biopsy may result.

The functional part may additionally comprise at least one electrical conductor which runs up into the rounded front side of the probe. The conductor may, for example, be melted into the probe and form a measuring electrode. At least one optical fiber may also be provided for spectroscopic measurements in the cell material, for example.

According to a further preferred embodiment of the invention, the probe body is formed by a linear, oblong form along a linear axis (capillary, tube, hollow needle) having a first end, which is the rounded front side, and a second end, which is connected to a reservoir device. The first end may comprise a rounding of the capillary wall (annular rounding) or the end of the probe body (spherical rounding). In these designs, the probe body is preferably a syringe needle having a free end at which the wall of the syringe needle is rounded. This embodiment of the present invention may have advantages because of its compatibility with conventional injection tools.

If the probe according to the present invention has a receiving tool on its free end, further advantages may result in the receiving or depositing of individual cells in cell material (e.g., cell cultures). The receiving tool has a receiving surface which is used as the substrate or carrier for at least one cell and has a concave or convex shape. A concave receiving surface may have advantages in regard to delimiting the receiving tool from the environment, such as from other probe parts or from cell material. The advantage of the convex receiving surface is its optimal adaptation to the displacing movement of the probe through the cell material according to the invention.

If, according to a variant of the invention, the receiving tool is positioned in a capillary-shaped probe or in a probe having a groove-shaped recess, providing a suspension or cultivation liquid in the environment of the receiving tool and the at least one cell located thereon is advantageously made easier.

Further advantages for depositing cells from the capillary or the groove-shaped recess result if the receiving tool is positioned displaceably in the probe.

Alternatively, the probe body may be formed by a molded body whose entire surface is rounded like the above-mentioned front side. The probe body may thus advantageously be moved through the cell material while enveloped completely by the cell material without mechanical connection to additional external devices. The probe body may, for example, be made completely spherical.

According to an alteration of this embodiment, the probe body may be formed by a spherical receiving tool having a rod-shaped holder, using which a advance force may advantageously be transmitted from a drive device to the receiving tool.

If the present invention is used for receiving or depositing cells on a cell carrier, e.g., having a cell culture, it may be advantageous if the probe is equipped with at least one spacer, using which the probe body may be placed on the cell carrier. The precision and stability of the positioning of the probe on the cell carrier may thus advantageously be increased.

If the probe body is equipped with at least one force element, advantages may result for the targeted and directed action of an external advance force. If the force element is a mechanical holder, advantages result in regard to the reliability and precision of the force transmission. If the force element comprises a magnetic element, contact-free manipulation of the probe in the cell material is advantageously made possible.

A further subject of the invention is a cell manipulator, particularly an operating device such as an injection, biopsy, and/or examination device for processing cell material, the cell manipulator comprising at least one probe according to the present invention and at least one drive device for moving the at least one probe. The cell manipulator has the special advantage that the probe may be manipulated in the cell material using the drive device with high precision and reproducibility. If the drive device comprises a piezoelectric drive, advantages result for the controllability of the probe movement. Alternatively, the drive device may be formed by a magnetic drive, through which advantages result in regard to contactless transmission of the advance force. Furthermore, the drive device may comprise a spring drive, so that advantages result in regard to an especially simple construction of the manipulation device.

According to preferred embodiments of the invention, the cell manipulator is equipped with a positioning device for controlling the drive device, a detector device for detecting the position of the at least one tool, and/or a carrier device for receiving cell material.

Preferred applications of the present invention are in vitro cell culture, tissue engineering in biotechnology, providing tissue models for pharmacology, and medical therapy.

BRIEF DESCRIPTION OF SEVERAL VIEWS OF THE DRAWINGS

Further details and advantages of the present invention will be described in the following with reference to the attached drawing.

DETAILED DESCRIPTION OF PREFERRED EMBODIMENTS

Figure 1:
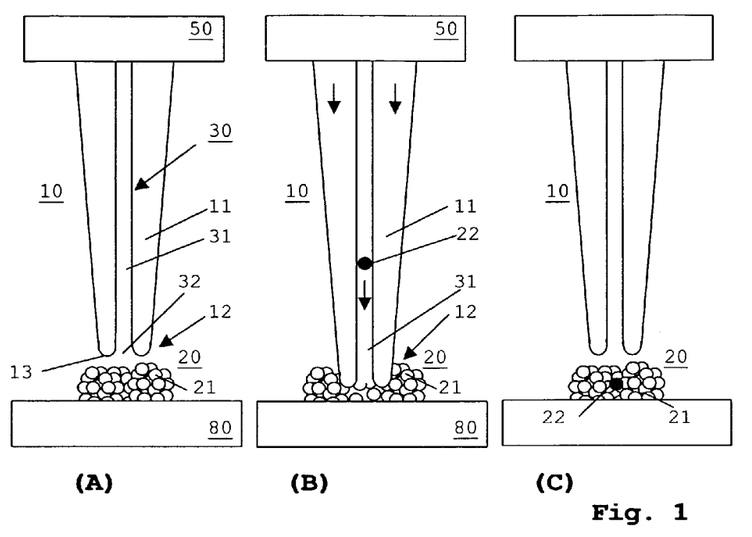
FIG. 1 shows the sequence of a cell injection corresponding to an embodiment of the method according to the invention.

The movement according to the invention of a probe through a cell material is shown in FIG. 1 in the example of the injection of a cell into a tissue sample. In the left part A of FIG. 1, a probe 10 according to the invention is illustrated in a schematic sectional view. The probe 10 comprises a probe body 11, which is formed by a hollow needle or pipette tip. The free end 12 of the probe body 11 represents the front side 13 having the rounded surface according to the present invention. A hollow channel 31 having an opening 32 at the end 12 runs in the interior of the probe body 11 as the functional part 30. The opposite end of the probe body 11 is connected to a piezoelectric drive device 50.

In a starting position (A), the probe 10 is located at a distance from a cell material 20, which is positioned on a carrier 80. The cell material 20 is, for example, a cell group or spheroid made of 50 to 500 adjoining cells 21, which are connected to one another via adhesion contacts. A stem cell is to be injected into the cell material 20 using the procedure described in the following, in order to incite this stem cell to a cell-specific differentiation in the cell material.

According to the middle partial figure B of FIG. 1, the probe 10 is shifted into the cell material 20, whereby the cells 21 of the cell material are displaced. As soon as the end 12 is seated on the cell material 20, adhesion contacts form with the cells 21. Under the effect of the permanently acting advance force of the drive device 50, the adhesion contacts are continuously rearranged, so that first the end and, with advancing propulsion, also the adjoining part of the probe body 11 are surrounded by the cells 21. During the movement of the probe through the cell material, the tool surface is continuously grown over by the cells 21.

When the end 12 is at a predefined distance (e.g., half the thickness of the cell group) from the carrier 80, the advance movement is stopped. A stem cell 22 is moved through the hollow channel 31 into the cell material 20 from a reservoir device (not shown). This movement is performed, for example, through flushing using a suspension liquid.

After the injection of the stem cells into the cell material, the probe 10 is pulled back. The retraction movement is also performed at a velocity so low that the cells 21 may rearrange themselves without injury until the displaced space around the injected stem cell 22 is filled again (partial image C from FIG. 1).

Alternatively to the design shown in FIG. 1, the drive device 50 may be attached to the carrier 80 and the relative movement may be generated between the cell material 20 and the probe 10 on the carrier side, while the probe 10 is positioned fixed.

Figure 2:
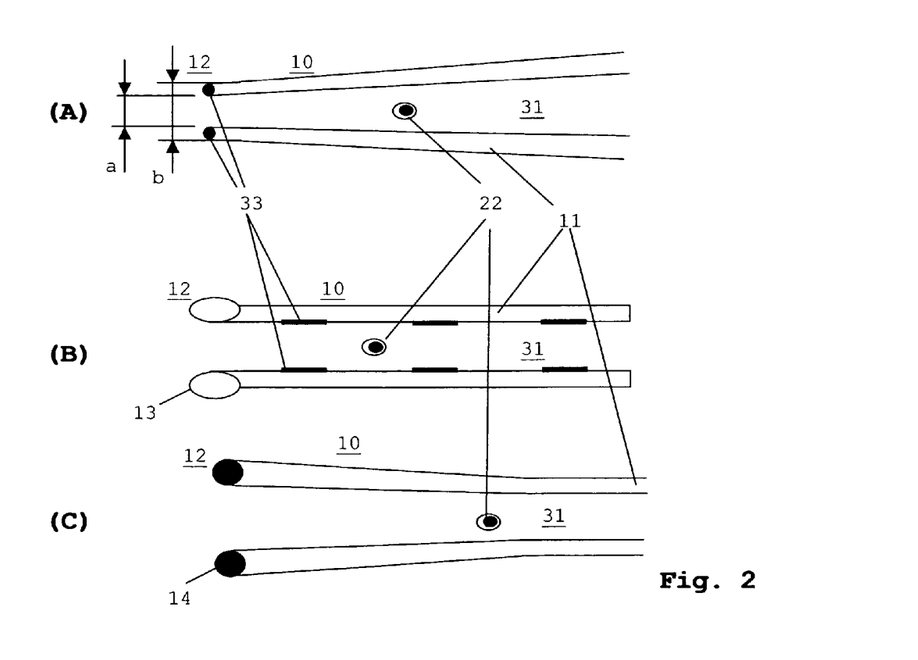
FIG. 2 shows different embodiments of probes according to the invention.

Further details of the free end 12 in different embodiments of probes 10 according to the present invention are illustrated in FIG. 2. Partial image (A) shows a conically tapering probe body 11. The displacement of cells in the cell material is advantageously favored by this shape. The front sides 13 are rounded in accordance with the principles explained above. The probe body 11 is made of glass, an inert metal (e.g., platinum), or an inert plastic material (e.g., polyimide), for example. The characteristic dimensions a (internal diameter of the hollow channel 31 at the opening 32) and b (external diameter of the probe body 11 at the end 12) are conventionally selected in the ranges a=10 µm to 100 µm and b=10.5 µm to 200 µm. Smaller dimensions in the range a=0.1 µm to 10 µm may be selected for the injection of especially small cells or of synthetic particles, or larger dimensions of, for example, a=100 µm to 5 mm may be selected for the injection of embryonic stem cells, for example, the dimension b being selected correspondingly larger in accordance with the wall thickness of the probe body 11.

The probe 10 may be equipped with a sensor 33. As shown in partial image (A), an impedance sensor 33 is provided on the end 12. The impedance sensor 33 comprises two semicircular electrodes (impedance electrodes), which are attached to the surface of the front side 13 through-vapor deposition, for example. Alternatively, the impedance electrodes may be attached to the outside of the probe body 11 on its end 12. The electrodes of the impedance sensor 33 are connected to a control device via electrical connection lines (not shown) along the probe body 11. As a cell 22 flows through the hollow channel 31, an impedance signal is generated by detuning the impedance between the impedance electrodes, which provides information about the number, size, and electrical properties of the cells passing by in a way known per se.

As shown in partial image (B), impedance sensors 33 may alternatively or additionally be provided on the interior of the hollow channel 31. Furthermore, partial image (B) shows a bulging front side 13 at the end 12 of the probe body 11, which is formed having a constant diameter.

As shown in partial image (C), the probe body 11 may expand conically toward the end 12. Partial image (C) of FIG. 2 schematically illustrates an adhesion-encouraging coating 14 on the end 12 of the probe body 11. This bonding coating is preferably only provided on the rounded, displacing front side of the probe 10, while the surface of the remaining probe body 11 preferably has an adhesion-reducing coating in order to encourage sliding between the displaced cells. The bonding coating comprises, for example, fibronectin. A silanization or a coating with biological macromolecules (such as PolyHema) may be provided for the adhesion reduction. The inner surface of the hollow channel may also be coated to reduce adhesion in this way.

The cross-sectional shape of the capillary-shaped probe body is preferably round. Alternatively, a flattened elliptical shape may be provided, which allows a preferred direction for the lateral movement in a movement direction perpendicular to the longitudinal axis of the probe body 11.

In the embodiment of the invention shown in partial image (D), the capillary-shaped probe body is cut diagonally on its free end 12, so that a scoop-shaped receiving tool 15 is formed. The inner wall of the hollow channel 31 of the capillary 11 forms a receiving surface 16 at the free end 12, which is delimited laterally by upright edges 17. For the intended use, the probe 10 is placed on a carrier 80 (e.g., floor of a culture carrier) or a cell material 20 located thereon. The probe 10 is advanced in the cell material 20 (see double arrow) until a desired cell 21 has been transferred to the receiving tool 15. The cell transfer may be encouraged by the natural intrinsic movement of the cell 21. As soon as the cell 21 has been received by the probe 10, it may be removed from the carrier 80 and moved to a target substrate.

As shown in partial image E, the probe body 11 of the probe 10 according to the present invention comprises a receiving tool 15 which is positioned at the end of a probe shaft. The receiving tool 15 has a spherical shape whose surface forms a receiving surface for a cell 21 to be transferred from a carrier 80. The receiving tool 15 has a diameter of 15 µm, for example.

As shown in partial image F of FIG. 2, the spherical receiving tool 15 may be combined with a capillary-shaped probe body 11. The receiving tool 15 is displaceable with the probe shaft 19 in the hollow channel 31 corresponding to the longitudinal axis of the capillary 11. To receive a cell 21, the probe 10 is immersed in a cultivation liquid 81 over the carrier and moved toward the cell material 20 located thereon. The receiving tool 15 is advanced using a drive device (see below), cell material 20 possibly being displaced without injury. The cells 21 may be transferred to the receiving tool 15 through the advance movement and possibly supported by the natural cell movement. Partial image F also illustrates the rounded shape of all parts of the free end 12 of the probe 10, so that this may be moved injury-free through cell material, completely corresponding to the method according to the present invention.

Further variants of a receiving tool 15 displaceable in relation to the remaining probe body 11 are illustrated in the partial images G and H of FIG. 2. The receiving tool is formed as a cylindrical plunger or cuboid slide, which is positioned so it is displaceable in the hollow channel 31 of the capillary 11 (partial image G) or in an open, groove-shaped recess 34 of the probe body 11 (partial image H). Particularly the embodiments of the probe 10 according to the present invention shown in the partial images F through H have the advantage that a liquid droplet 81 may be formed on the probe 10 as a protection for cell material on the probe 10.

A shell-shaped or spoon-shaped design of the free end 12 of the probe 10 is illustrated in partial image I. A receiving tool 15 in the form of a part of a hollow sphere, on whose interior the receiving surface 16 for at least one cell 21 is provided, is formed at the end of the probe body 11. An opening 17, through which the cells 21 may be received, is located on the floor of the receiving tool 15. The receiving is performed by moving the probe 10 in relation to the carrier 80, possibly supported by the natural cell movement of the cells 21. In an altered design, the opening 17 may be dispensed with and instead cell material may be received in the receiving tool 15 via its top.

Partial image J of FIG. 2 shows spacers 18, which may be provided in any of the probes according to the invention at the free end 12 or another position of the probe body 11 in order to make positioning on the carrier 80 easier. A special advantage is that the displacement movement of the probe 10 through cell material according to the invention may also be performed using the spacers 18, without cells being injured in an undesired way.

The diameter of the receiving tool 15 shown in the partial images I and J is, for example, 0.2 mm. The diameter of the opening 17 may be, for example, 1 μm to 0.5 mm.

The partial images K and L illustrate that the present invention may be used not only for receiving individual cells, but rather also for transferring cell material, such as cell monolayers or cell cultures 20. As shown in partial image K, for example, a scoop-shaped receiving tool 15 is provided which is shaped analogously to partial image D and is provided at the end of a tubular or box-shaped probe body, for example. The width of the receiving surface 16 is, for example, 10 μm to 50 mm. The lateral edges 17 cause a delimitation of the cell material received from the carrier 80 from its environment. Partial image L shows the insertion of the probe 10 into a multilayer cell system or tissue composite, in order to lift a layer of cells (cell layer 24) out of this without destruction and without a biochemical treatment. The tool is advanced (see arrow) at the cited physiological reference velocity of the cells.

Figure 3:
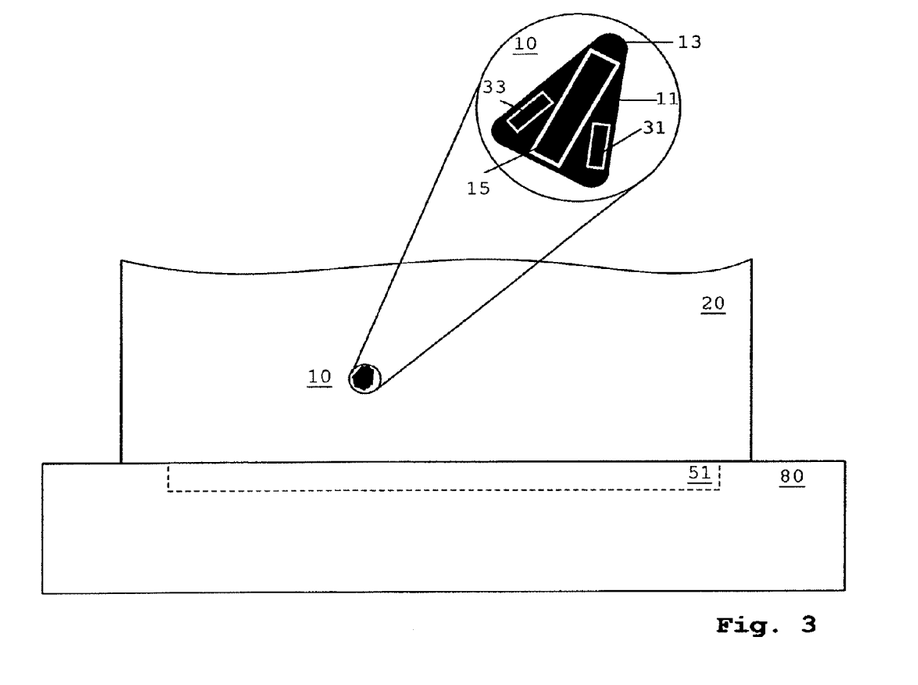
FIG. 3 shows an altered embodiment of a probe according to the invention.

FIG. 3 shows an altered embodiment of the present invention, in which the probe 10 (illustrated enlarged above) is completely enclosed externally by cell material 20, without a mechanical connection. The cell material 20 is positioned on the carrier 80, in which a magnetic device 51 is integrated as the drive device. The probe 10 has a cone-shaped probe body 11 having rounded areas 13 at the adjoining surfaces. The rounded areas form multiple front sides in this case. A permanent magnet 15 is integrated in the probe body 11 as the force element. By producing suitably shaped magnetic fields using the magnetic device 51, which contains a coil arrangement for magnetic field generation, for example, the probe 10 may be moved in a directed way through the cell material 20. Furthermore, drifting of the probe 10 under the effect of intercellular forces may be provided.

The reference number 31 refers to a cavity in the probe body 11 which is filled with an active ingredient, for example. The active ingredient may exit at desired positions in the cell material 20 through an opening or a permeable wall of the probe body 11. The reference number 33 relates to a sensor which is integrated in the probe 10. The sensor 33 comprises, for example, a pH sensor, glucose sensor, or another sensor for biologically relevant properties (biosensor).

According to the invention, the probe 10 shown in FIG. 3 may temporarily be connected to an external reservoir in order to refill the cavity 31 with an active ingredient, for example. For this purpose, for example, in accordance with the principles explained above, a capillary-shaped probe is moved through the cell material 20 up to the probe 10 and coupled thereto. Analogously, an electrical stimulator having an electrical power reservoir may be positioned in the probe 10 as a functional unit, which is connected as needed to an external voltage source via electrical lines. This connection is performed by inserting electrical lines in accordance with the displacement movement according to the present invention.

Figure 4:
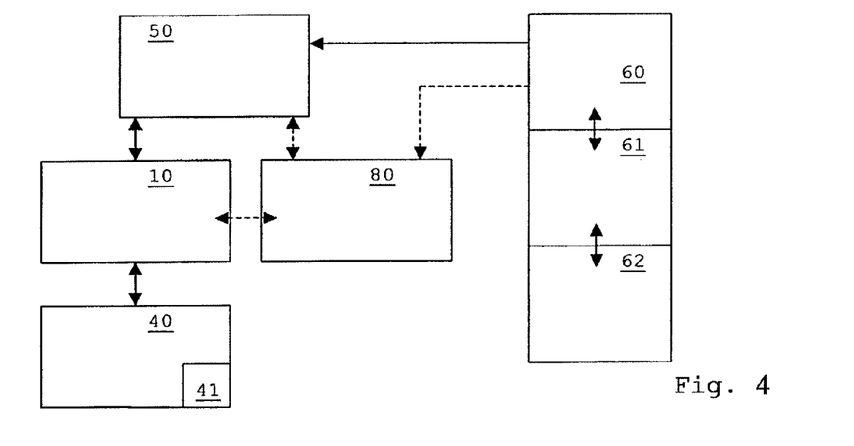
FIG. 4 shows a schematic illustration of a cell manipulator according to the invention.

As shown in the block diagram in FIG. 4, a cell manipulator according to the invention comprises at least one probe 10 and at least one drive device 50 for exerting an advance force on the probe 10. The drive device 50 contains, for example, piezocrystals, using which the probe 10 is positionable and movable, analogously to micromanipulator systems known per se, in different spatial directions at a precision of <100 nm. The operating path of the probe 10 may be between 0.1 mm and several centimeters.

The drive device 50 is connected to a positioning device 60. The positioning device 60 is a mechanically stable component, which may be fixed at micrometer precision in relation to the target cell system (cell material), and which allows the required slow movement of the probe into or out of the target cell system to be produced. Its object is to guarantee the stable position of the entire injection system in relation to the target cell system over the duration of the manipulation (hours, days, or even weeks). This may be achieved via an adjustable three-point mounting on the culture system (see FIG. 5) or anchoring, e.g., to the bones of the skull for cell injection into the brain. Alternatively, if the drive device 50 is adapted for moving the carrier 80 of the cell material, the positioning device 60 may also be connected to the carrier 80 (see dashed arrows). The carrier 80 is, for example, a culture dish (see FIG. 5) or a substrate in a cultivation system.

Furthermore, the positioning device 60 is connected to a control device 61 and a measuring and display device 62. The control device 61 is used for controlling the entire system and contains a processor or computer. The current and planned positions are detected via sensors (strain gauges on actuators, 4-quadrant detection using laser beam as in atomic force microscopy or in an analogous way). The information is processed using software and presented in such a way that the real and planned movements are shown on a monitor together with expedient parameters. For this purpose, a camera system having microscopic enlargement and a zoom function may be provided.

The probe 10 is preferably connected to a sample reservoir 40, which contains a transport system 41 for moving a sample from the reservoir 40 into the probe 10. The sample to be injected into the cell material is, for example, a cell suspension. The transport system 41 is a conveyor device known per se, such as a precision injection pump. The sample reservoir 40 for receiving the cells to be injected may be a Hamilton syringe or a container connected via a 3-way system having a low dead volume. The transport system 41 presses a cell suspension into the injection tool (probe 10) via mechanical compression, for example. In this case, very low volumes are to be moved (velocity a few μm/minutes). Washing procedures may also be performed using wash solutions (velocity 1 to a few hundreds of μm/seconds). This may be achieved via programmable injection pumps.

Figure 5:
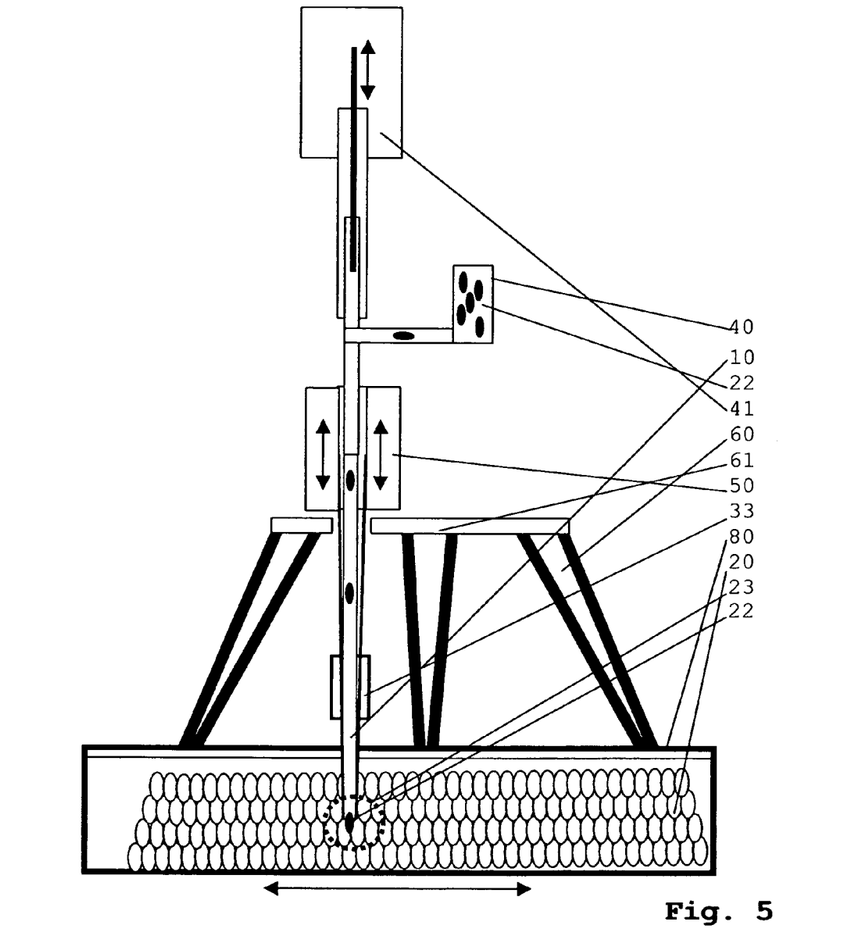
FIG. 5 shows an illustration of further details of an embodiment of a cell manipulator according to the invention.

Further details of the cell manipulator are shown in FIG. 5 in the example of an in vitro system for biotechnology (tissue engineering). The goal is to inject one or more cells 22 from a cell reservoir 40 into a cell tissue composite 20 using a microcapillary (probe 10). The probe 10 is connected via a channel system to the cell reservoir 40. Simultaneously, the probe 10 is connected to a Hamilton syringe (transport system 41 for the cell suspension 22), which is addressed via a processor or a computer controller (not shown). The entire system is located on an operating platform 63, which may not move in relation to the tissue composite 20, since it is connected fixed to the culture dish 18 via the positioning device 60.

The basic adjustment of the operating platform 63 is performed using the positioning device 60. A piezotube, which may extend or shorten in the way specified and thus inserts and/or pulls the probe 10 into and/or out of the tissue composite 20, is used as the propulsion system or drive device 50 for the probe 10. A target cell region 23 (dotted ring), into which precisely one cell 22 is introduced, is shown. A single cell detector system 33, using which the number of the injected cells may be detected (shown here as an optical system), is located on the shaft of the capillary probe 10.

The cell manipulator corresponding to FIG. 5 is actuated as follows. In a first step, the positioning device is brought into a fixed connection with the target tissue 20. This is performed by fixing the positioning device on the culture dish 80 or on the surface of an organism or a suitable part of the skeletal frame. In a second step, the microinjection tool 10 is attached to the operating platform 61 and coarsely pre-adjusted, so that its tip is localized shortly in front of the target tissue or cell system 20. In the next step, the capillary of the probe 10 is filled with the nutritional solution, a physiological solution, or another suitable fluid and guided up to the cell tissue until it makes contact. The programmed advance of the microinjection tool then occurs corresponding to a velocity of, for example, less than 1 μm/h up to a few hundreds of μm/h, until the target region 23 has been reached. Either at this time or earlier, the cells to be injected are flushed out of the reservoir into the microinjection tool and detected, counted, and possibly characterized via the detector as they pass the inserted part. By moving the injection tool in all three spatial directions at the above-mentioned low velocity, the system may be guided into a new target region, so that cells may be positioned three-dimensionally in the tissue in a previously determinable way. After completed injection, the microinjection tool is removed from the target tissue again. The low velocity, which is also referred to as "physiological velocity", allows the cells of the tissue at the tip of the injection tool to detach the cell adhesion contacts, so that the cells are displaced in an orderly way, but are not injured.

Figure 6:
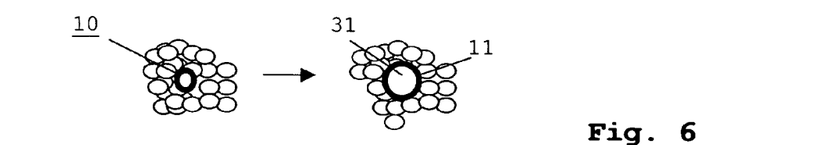
FIG. 6 shows an illustration of a radial expansion movement of a probe.

FIG. 6 shows an example of a radial expansion movement of a capillary-shaped probe 10, whose probe body 11 is made of an elastic material (such as plastic, rubber) or a non-elastic expandable material (such as lamellae made of steel or plastic or the like which are displaceable in relation to one another). By increasing the pressure in the hollow channel 31 of the probe 10, its diameter may be expanded, the cells being displaced without injury. The diameter of the probe body 11 increases at the advance velocity described above.

Figure 7:
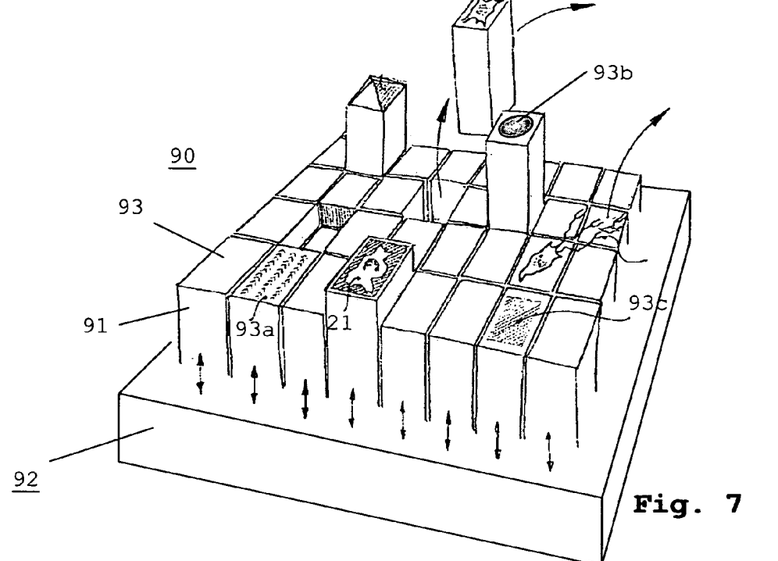
FIG. 7 shows a further altered embodiment of a probe according to the invention.

FIG. 7 shows an exemplary embodiment of multiple probes 91 used according to the present invention, which form a manipulation tool 90. The probes are shaping elements 91 of the manipulation tool 90, each of which is displaceable individually using a drive device 92, which is attached to a base part (not shown). Each shaping element 91 has an oblong cuboid shape having a top 93. The total number of the tops 93 form the surface of the manipulation tool 90, which is used to remove individual cells from the cell material 20. The shaping elements 91 form a tool body. The tops 93 have conventional dimensions in the range from 0.01 mm to 5 mm. They are flattened ("infinite" radius of curvature) and possibly have rounded edges. The shaping elements 91 are oriented so that the tops 93 form a matrix arrangement made of linear rows and columns. The shaping elements 91 are displaced in relation to the base part, for example, using positioning motors or piezoelectric drives. The tool surface is structured depending on the selected advance of a shaping element 91. Individual shaping elements 91 may be separable from the drive device 92 in order to remove cells.

For the removal of cells 21 from a cell material according to the invention, this cell material is first positioned on the tool surface, i.e., the totality of the tops 93. For this purpose, for example, growth from a cultivation medium in a culture vessel is provided. Only individual cells 21 are shown in FIG. 7 for reasons of clarity. Cells which are to be removed from the cell material are subsequently observed and selected. The shaping elements 91 corresponding to the selected cells are advanced. This advance occurs at the above-mentioned physiological reference velocity, so that injury-free displacement and separation of the selected cells occurs. Subsequently, the shaping element having the cell may be detached from the manipulation tool 90. Depositing a cell 21 on a cell material according to the present invention may be provided analogously using the reversed step sequence.

FIG. 7 also illustrates that the individual tops 93 of the shaping elements 91 may be made differently in order to additionally modify the cell material at the particular positions. For example, microstructures (see at 93a) may be provided for improving the adhesion capability of the top 93 or additional structure elements may be provided, such as a bulge 93b formed on the inside of the shaping element 91 for improved separation of the cell from the surrounding cell material. Furthermore, all or individual shaping elements 91 may have an adhesion-increasing coating 93c.

Figure 8:
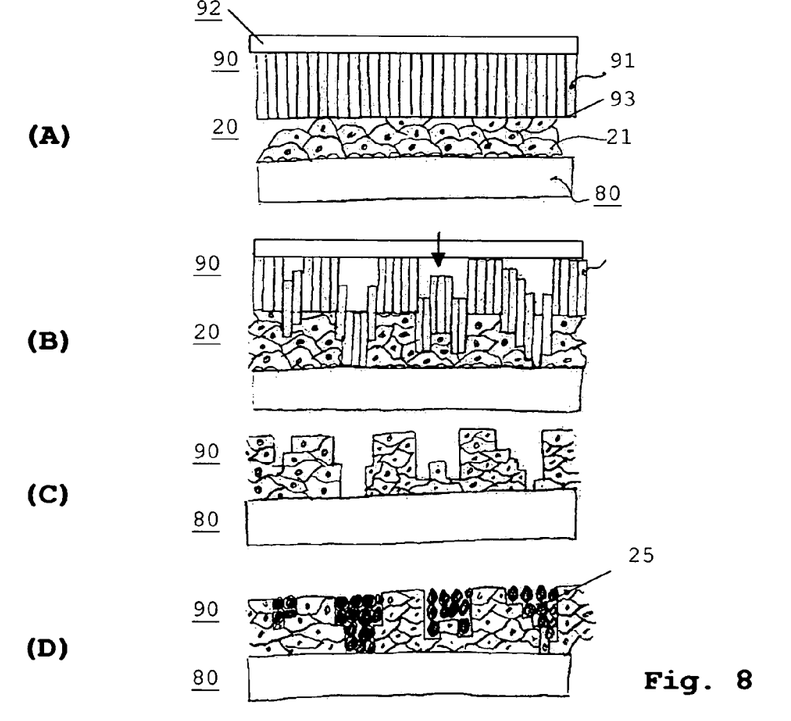
FIG. 8 shows the sequence of cell shaping corresponding to an embodiment of the method according to the invention.

Alternatively, a manipulation tool 90 as shown in FIG. 7 may be used as an impression tool, as is shown in the image sequence in FIG. 8. In a starting situation as shown in partial image A, a cell material 20 is located on a carrier 80, through which a tool is to be guided corresponding to the method according to the present invention. The manipulation tool 90 having multiple displaceable shaping elements 91 is positioned over the initially free surface of the cell material 20. The manipulation tool 90 is moved toward the cell material 20 until the tops 93, which point downward in this case, contact the cell material 20. Subsequently, as shown in partial image B, the surface of the manipulation tool 90 is adjusted through the targeted advance of individual shaping elements 91. The propulsion movement is performed at the above-mentioned physiological reference velocity of biological cells. The individual shaping elements 91 displace the cells in the cell material without injury.

Subsequently, as shown in partial image C, the manipulation tool 90 is removed. The surface shape of the tool remains as a complementary structure in the cell material 20. To make it easier to separate the manipulation tool 90 from the cell material 20, the tops 93 of the shaping elements 91 may be provided with a coating on which adhesion of cells is suppressed. The coating is performed, for example, using the polymers Polyhema or PTFE. Finally, the gaps embossed in the cell material may be filled with other cells or a synthetic matrix material 25 as shown in partial image D.

The selection of the shape and cells or additives 25 possibly supplied into the cell material is performed depending on the concrete object in the scope of the tissue engineering. Using the sequence shown in FIG. 8, for example, epithelial cells having a predefined structure may be brought into contact with tissue cells.

The features of the invention disclosed in the above description, the claims, and the figures may be of significance both individually or in combination for implementing the present invention in its various embodiments.

The invention claimed is:

1. A method for moving a probe through an aggregate of biological cells or tissue which are connected via adhesion contacts or an organ comprising:

inserting a probe into the aggregate of biological cells or tissue which are connected via adhesion contacts or an organ at an advance velocity of 0.1 to 500 µm/hour, wherein the tip of the probe has a radius of curvature selected from the group consisting of larger than 10 µm and less than 5 mm;

wherein the probe displaces the aggregate of biological cells or tissue which are connected via adhesion contacts or an organ without injuring any of the cells and the macromolecular bonds running between the adhesion contacts of the biological cells are separated and relinked to the probe surface.

2. The method according to claim 1, wherein the probe displaces the biological cells without injuring any of the biological cells such that adhesion contacts between the biological cells reversibly detach in an environment changed by the moving probe.

3. The method according to claim 1, wherein the probe is subjected to an advance force comprising at least one force selected from the group consisting of mechanical pressure forces, electrical forces, magnetic forces and intercellular forces.

4. The method according to claim 1, wherein the probe is moved through an aggregation formed from biological cells comprising a composite material made of the biological cells or the biological cells and a matrix material.

5. The method according to claim 1, wherein the probe has an oblong shape having a longitudinal direction and is moved in a direction parallel to the longitudinal direction.

6. The method according to claim 1, wherein the probe is hollow, and further wherein a substance is supplied into the aggregation formed from biological cells using the probe.

7. The method according to claim 6, wherein at least one biological cell is supplied into the aggregation formed from biological cells using the probe.

8. The method according to claim 7, wherein the at least one biological cell is supplied into the aggregation formed from biological cells in a frozen state.

9. The method according to claim 7, wherein cell locomotion of the at least one biological cell contributes to moving the at least one biological cell from the probe into the aggregation formed from biological cells.

10. The method of claim 6, wherein the substance is supplied into a cell.

11. The method according to claim 1, wherein at least one biological cell is removed from the aggregation formed from biological cells using the probe.

12. The method according to claim 11, wherein cell locomotion of the at least one biological cell contributes to moving the at least one biological cell from the aggregation formed from biological cells to the probe.

13. The method according to claim 1, wherein properties of the aggregation formed from biological cells are detected using the probe.

14. The method of claim 13, wherein the properties of a cell are detected using the probe.

15. The method according to claim 1, wherein the aggregation formed from biological cells is shaped using multiple probes, each of which forms a shaping element of a manipulation tool.

16. The method according to claim 1, wherein the probe is moved through aggregation formed from biological cells outside an animal or human.

17. A method for moving a probe through an aggregate of biological cells or tissue which are connected via adhesion contacts or an organ, wherein the tip of the probe has a radius of curvature selected from the group consisting of larger than 10 µm and less than 5 mm, comprising:

moving the probe through the aggregation formed from biological cells at an advance velocity in a range from 0.1 µm/h to 500 µm/h;

displacing the biological cells with the probe without injuring any of the biological cells; and transferring at least one biological cell from the probe to the aggregate of biological cells or tissue which are connected via adhesion contacts or an organ or from the aggregate of biological cells or tissue which are connected via adhesion contacts or an organ to the probe, wherein cell locomotion of the at least one biological cell contributes to the transferring, wherein the probe is moved through an aggregate of biological cells or tissue which are connected via adhesion contacts or organ which are outside an animal or human wherein the probe displaces the aggregate of biological cells or tissue which are connected via adhesion contacts or an organ without injuring any of the cells and the macromolecular bonds running between the adhesion contacts of the biological cells are separated and relinked to the probe surface.

18. A method for moving a probe through an aggregate of biological cells or tissue which are connected via adhesion contacts or an organ, wherein the tip of the probe has a radius of curvature selected from the group consisting of larger than 10 µm and less than 5 mm, wherein:

the probe is moved through the aggregate of biological cells or tissue which are connected via adhesion contacts or an organ at an advance velocity in a range from 0.1 µm/h to 500 µm/h; and the probe displaces the biological cells without injuring any of the biological cells, wherein the macromolecular bonds running between the cells are separated and relinked to the probe surface, and further wherein the probe is moved through an aggregate of biological cells or tissue which are connected via adhesion contacts or an organ outside an animal or human.

19. A method for moving a probe through an aggregate of biological cells or tissue which are connected via adhesion contacts or an organ comprising:

inserting a probe into the aggregate of biological cells or tissue which are connected via adhesion contacts or an organ at an advance velocity of 0.1 to 500 µm/hour, wherein the tip of the probe is scoop shaped with a width of 10 µm to 50 mm;

wherein the probe displaces the aggregate of biological cells or tissue which are connected via adhesion contacts or an organ without injuring any of the cells and the macromolecular bonds running between the adhesion contacts of the biological cells are separated and relinked to the probe surface.

* * * * *